Nov. 11, 1941. R. W. MUNRO Re. 21,943

MEDICAL DEVICE

Original Filed Jan. 30, 1936

Inventor
RUTH W. MUNRO
by Victor L. Cameron
Attorney

Reissued Nov. 11, 1941

Re. 21,943

UNITED STATES PATENT OFFICE 21,943

MEDICAL DEVICE

Ruth W. Munro, Winchester, Mass.

Original No. 2,110,962, dated March 15, 1938, Serial No. 61,555, January 30, 1936. Application for reissue March 2, 1940, Serial No. 321,980

22 Claims. (Cl. 128—271)

This invention relates to means for simultaneously isolating, protecting, and sterilizing certain internal body organs, and particularly relates to the devices usually referred to as pessaries, suppositories or tampons. It is a continuation and development of and improvement upon the subject matter of my Patent No. 2,049,-270. Broadly my invention comprises means for isolating and protecting an internal organ from dangerous or undesired matter, means for collecting or entrapping and sterilizing any matter present in surrounding regions which it is desired should not reach the organ to be protected; or means for collecting secretion from one of said organs and preventing its entrance into the other organ; means for sterilizing the organ and surrounding regions; means if desired for supporting said organ; and means for self-positioning the said isolating, sterilizing and supporting device in proper relation to said organ to be protected.

For example, the uterus is an internal body organ from which there is at certain periods a normal discharge through its mouth or cervix, and through which mouth other matter may find its way from the vagina into the uterus. In such connection my device finds a field of great usefulness. It may also be used in the rectum to shut off, protect and sterilize portions of the rectal passage, and adaptations of the same device may be used in the urethra, though in this case a physician's services usually are required. It may also be of value in operations on the nose, throat and ears, its combined isolating, protecting and sterilizing properties having many possibilities of usefulness. In its several uses its design necessarily will be changed so that it may be inserted and retained in effective position, but in all forms, the elements providing isolation, protection and sterilization of some predetermined body organ are present.

In many cases the menstrual flow is accompanied with much irritation of the vagina and more or less suffering, resulting in part at least from improper drainage. This is frequently the case where there is any displacement of the uterus or other organ. Furthermore, the walls of the vagina are extensible and full of creases and folds into which the secretions and other matter enter, and which for obvious sanitary reasons, it is important to sterilize and disinfect. Most commonly it is attempted to secure this result by douches, in which not infrequently there is used, particularly by the unadvised or poorly advised, harsh chemicals, many of which are on the market advertised for this purpose, and which may cause serious injury to the delicate membranes. Even douches are frequently omitted on account of the difficulty or lack of opportunity of taking the same, with extremely unfortunate results. In lieu of douches, suppositories of various types are coming into increasing use. These sterilize the vagina to some extent but have no capacity either of protecting the vagina from matter flowing from the uterus or sealing the cervix against the entry into the uterus of undesired matter, both of which my invention may provide.

My device moreover is more satisfactory than douches in that there is no heat or cold to affect the patient. My pessary or like device may be made of soluble, partly soluble, or insoluble material. If of soluble material, the same is molded in desired form and, because of the medicament contained therein, its contact with all adjacent members is disinfecting, sterilizing, medicative and deodorizing in nature. These results increase as the device dissolves, but it is designed to melt so slowly that before it has melted to the extent that its isolating and holding capacities are ended, its sterilizing action is complete or well advanced. Such substances as gelatine, glycerine, or paraffin are satisfactory in use, though I prefer to use a material which upon dissolution will be absorbed by the body tissues so that no residue is left to collect in the vagina. The fact that nothing remains to be removed is an important advantage of the soluble form of my invention.

If made of partially soluble material, the pessary retains its sealing and holding characteristics throughout its period of use, while the soluable portions thereof melt and sterilize surrounding bodies and regions and entrapped matter. It may be retained for any desired period but usually by the time all the soluble material has melted, the period of danger has passed.

If of insoluble material, the device may be retained as long as desired, and extraneous disinfecting or sterilizing matter carried or injected into the vagina.

If my device is used to receive or to drain off menstrual flow, ordinarily the insoluble or partially soluble forms are used. In such case, the same may be packed with gauze or other material to absorb the moisture if desired. If used to protect the uterus from the entry of undesired matter and to sterilize such matter, preferably the entirely soluble form is used, although if it is desired at the same time to support the uterus or distend the walls of the vagina, the partially soluble form may be employed to great advantage.

The partially soluble embodiment may comprise a flexible or inflexible body of desired contour, which may be entirely coated, internally and externally, with a material which dissolves slowly at body temperatures, such as certain gelatin. Instead of coating the same, if preferred, my pessary may be made with pockets in its surfaces filled with medicated substances which dissolve or are freed at body temperatures. These pockets may be inside or outside or both. As the pessary substantially fills the vaginal passage, pockets in the outside of the same are likely to entrap any matter which may escape past the edges of the pessary.

Depending upon its use, my pessary may be so constructed as to provide an isolating or sealing member adapted to shut off the cervix to surrounding areas, or it may be constructed so as to connect the cervix with the mouth of the vagina and shut off the vagina. In this latter use, its bottom may be closed, and the device collect the menstrual flow. In this case it may be desirable to make some portion of my device of extensible material so that in cases where it may be inconvenient to remove the same, the device will expand to receive additional amounts of secretions.

As a further modification my device may be made of textile gauze or other fibrous material treated with medicament and coated with soluble gelatine or the like, and molded to desired form. Upon the melting of the gelatine the gauze, or if desired a sponge-like material, is freed and absorbs the moisture. In this case, as the device must be removed, a cord, tape or strip of gauze may be incorporated in the device to extend through the entrance to the vagina and by which the device may be removed if and when this is desired.

In all cases, my device tends to distend the walls of the vagina, relieving pressure against the cervix, reduces nervous tension and causes a relaxed condition. If desired, it may contain drugs to alleviate pain. The gelatinous or other soluble material acts as a lubricant and allays inflammation. If extension of the vagina is particularly desired, some soluble sponge-like material or a soluble gelatinizing material such as tapioca or sago may be incorporated in my device and the same when released will expand or swell and distend the walls of the vagina. While both of these materials will initially expand when released in the vagina under the action of the secretions of the vaginal mucosa, yet both ultimately will liquefy so that no solid or fibrous matter will remain to be removed from the vagina. The metal and hard rubber bogies sometimes used to extend the vagina frequently cause inflammation and have been known to cause peritonitis.

Another field of usefulness of my device lies in the case of operations or treatment of some single part or area either within the vagina, uterus or other organ. My device may be constructed with openings to any desired area and, particularly in the soluble or partially soluble forms will disinfect and protect surrounding areas so that no infection will spread and the treated area will be protected from dangerous matter which otherwise might reach the same. The yielding nature, flaccidity and creases and folds in the vagina make it difficult to get access to diseased parts and thus handicap accurate incisions. By inserting my device, which may be made in suitable shapes for treatment of cervix, cervical canal and uterus, also for protecting the vagina and cervical canal while treating the uterus, the organs may be distended, supported and disinfected, and if of hollow construction, a predetermined opening may be made in the same, permitting ready access to the part to be treated and insertion of instruments, acids, drugs, etc. Also, medicine or cauterizing and strong solutions, powders, gas, may be included in the suppository in cells formed in the suppository or otherwise as desired, with soothing, coating and counterirritants in remaining parts. My pessary may be used to promote healing and prevent infection after operations, etc., and may also be used to drain certain parts while protecting other parts from irritation and infection.

If desired, the insoluble form of my device may be filled with ice and used as an ice bag, in which case, it may be open at top and closed at bottom, or if of type usually open at bottom, the bottom may be plugged, or the device may be filled with a fluid which produces effect of ice or heat, or the whole pessary made of such material.

To adapt the pessaries to the individual patient as well as to certain uses, in certain types of the same, usually of permanent nature, certain portions may be made extensible or compressible, provided there be some definite rigid members about which or upon which the more variable parts may be supported. If desired it may be air-cushioned in part, or air may be incorporated in the sponge-like texture of the whole if the pessary be made of such material. In this case, the relatively hard but soluble coating on the spongy body of the pessary will make it sufficiently rigid to maintain its shape prior to insertion and to aid ready insertion, but as soon as this coating melts, the pessary, by reason of its flexible, spongy nature will readily conform to the size or shape of the vagina in which it is used. If, as above indicated, the sponge be of soluble material, then, like the solid but wholly soluble pessary, it will gradually melt and release medicament to sterilize the surrounding areas. It may also be constructed so as to permit ready insertion and expansion once in position as by fluting the same in whole or in part.

My suppository is capable of a great variety of uses and may be made of almost any shape and material desired, provided the main objectives of my invention be retained, that is, the isolation, sterilization and protection of one organ or a portion thereof, and the sterilization of surrounding organs and/or regions of undesired matter.

In the drawing I have illustrated and in the specification disclosed several practical embodiments of my invention. In the drawing.

My pessary comprises a head portion of generally spherical contour provided with a cup-shaped recess or recess 2 on the upper portion substantially diagonally of the pessary or angularly of the longitudinal axis thereof, which recess is adapted to receive the cervix or other organ, and above which extends a tangential portion or horn 3 adapted to fill the fornix or similar passage so as to prevent the entrance thereinto of matter from the cervix or vagina. The cup 2 may be round or oval, centered or non-centered, as desired.

Figure 1:
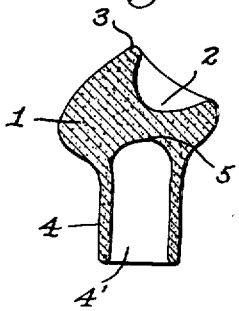
Fig. 1 is a sectional view of one of my completely soluble pessaries.
Figure 2:
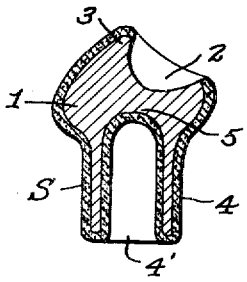
Fig. 2 is a similar view of a pessary which is partially soluble.
Figure 3:
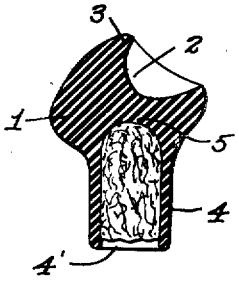
Fig. 3 shows a wholly insoluble pessary with a packing.

Integral with the head portion 1 is a cylindrical or tubular portion 4. As shown in Figs. 1, 2 and 3, this cylinder 4 is centrally located on the lower concaved side of the head portion. Pressure of the vagina walls on the device as it is inserted causes the pessary to reform in this zone, thereby adapting it to use in vaginas of varying sizes and shapes. This member 4 may be closed to the cup 2 and open at its opposite end 4′ as in Figs. 1, 2 and 3, or may be open to the cup 2 and closed at its lower end $4^2$ as in Figs. 4, 5 and 6. The cup 2 and cylinder 4 may both have communicating recesses as in Figs. 8 and 9, or the cylinder may be solid as in Figs. 7 and 11.

In the first case, the device is intended to isolate the cervix by enclosing the same with the cup 2, and to entrap matter present in the vagina with the recess in the cylinder 4, in which the same is retained until the pessary has either in whole or in part dissolved. The gradual melting of the soluble medicated material of which my pessary is in whole or in part composed sterilizes all surfaces with which the same comes in contact, and the dissolved substance enters all regions adjacent the organ to be protected and sterilizes all matter within the same, as well as any matter which may have entered the recess in the cylinder 4, and this sterilizing continues until the walls of the device collapse if the same is of entirely soluble nature, or until the soluble portion thereof dissolves.

If the open ended type of my invention is made of durable material, such as rubber, aluminum or the like, completely covered or partially covered with a layer S of medicated soluble material, the foreign matter entrapped in the cylinder 4 is never released in the vagina, and any such matter as may have found its way past the cylinder wall which substantially fills the vagina, has been subjected to the sterilizing effect of the freed medicament contained in the layer S of soluble material on the outer surface of the cylinder 4.

If the wholly insoluble type is used, sterilizing matter may be inserted by douche or suppository and because of the substantially complete isolation of the cervix by reason of the portions 2 and 3, there is but slight danger of any undesired matter reaching the cervex. However as the pessary of Fig. 1 entirely dissolves and is absorbed by the tissues of the vagina and other organs, whereas the insoluble portions of Figs. 2 and 3 have to be removed, the form of Fig. 1 is generally preferred. There are uses however, for example, where continued support for the uterus or expansion of the vagina walls are involved when the insoluble forms are more desirable.

Figure 4:
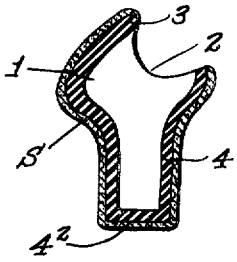
Fig. 4 shows a partially soluble pessary with its lower end closed.
Figure 5:
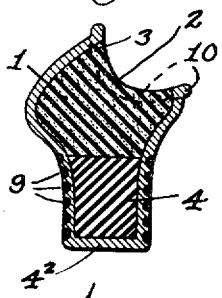
Fig. 5 is a view of a pessary having an extensible portion and provided with moisture entrapping pockets.
Figure 6:
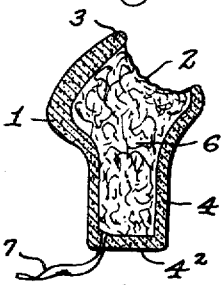
Fig. 6 is a closed end pessary having a packing.

In case my device is designed as in Figs. 4, 5 and 6 to entrap and collect menstrual flow and to prevent the same from entering the vagina and filling the creases and folds in the walls thereof, the wall 5 separating the cup 2 from the hollow cylinder 4 is omitted and the outer end of the cylinder closed as at $4^2$. In such case, I prefer to use the only partially soluble or insoluble construction. Furthermore, in such cases, it is of advantage to make the portion 2 of extensible material to receive increasing quantities of secretion as of rubber as indicated in Fig. 5. Similarly the portion 4 may be made extensible if desired. This characteristic however need not prevent the device from being covered with the soluble medicated substance S, which as it melts will disinfect and sterilize the regions adjacent the cervix and in the interior of the vagina.

It is possible however to use the wholly soluble form successfully for such purpose, particularly if there be sealed therein a sponge, gauze or other absorbent material 6 as shown in Fig. 6, in which case, there may be incorporated in the pessary a tape or strip of gauze 7 by which the sponge or other body may be removed.

It will be understood that also in the forms of Figs. 1, 2 and 3, or any other form capable of receiving the same, packings of gauze or like absorbent material 6 may be inserted, or any of my devices may be made of gauze or similar material, saturated with sterilizing matter, and moulded to desired form with or without a covering layer of glycerine or gelatin S.

The wholly soluble pessary may be satisfactorily made of gelatin, glycerine or like substances slowly melting at body temperatures. The partially soluble forms may be completely covered with such material or may be constructed with pockets or cells filled with such material as shown at 9, Fig. 5, which material will be released as the seal of gelatin or other substance melts. The medicament of drug may be mixed into the body of glycerine or gelatin, or may be contained only in certain portions thereof as in cavities or cells in the body of the walls. This is all incidental to the principal invention and improvements as herein set forth.

Figure 7:
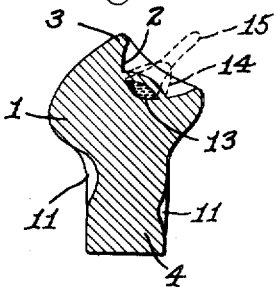
Fig. 7 is a view of a pessary showing in dotted lines alternate constructions for different uses.

All of my devices may be provided with reinforcing positioning flanges 10 as shown in Fig. 5, or the surfaces of the devices may be concaved or hollowed as at 11 in Fig. 7 to receive portions of the vagina walls whereby the device is held in position.

Figure 8:
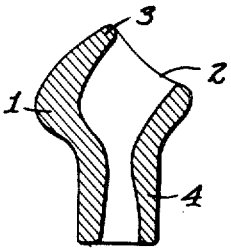
Fig. 8 shows a pessary having a passage throughout.
Figure 9:
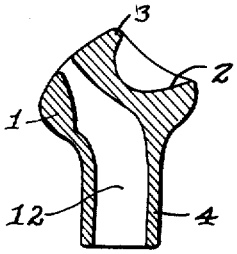
Fig. 9 shows a pessary having an opening to a part to be treated.
Figure 10:
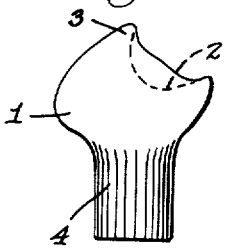
Fig. 10 shows a pessary having a fluted extensible cylinder.

The device of Fig. 8 is hollow throughout and the opening in its upper end affords access to the cervix. It will be understood that there may be an opening at any predetermined point. By means of such a device an instrument may be inserted or drugs or swabs applied to isolated parts as to the vagina wall through the opening 12 in Fig. 9. Meanwhile the rest of the vagina or other organ is protected and simultaneously sterilized or otherwise treated with material as desired. Such a device may also be used to sterilize the vagina when it is not desired to isolate the cervix.

If it is desired only to sterilize the vagina the pessary may be made of solid soluble material, formed only with the cup shaped recess 2, the horn 3 and cylinder 4. If in addition, it is desired to use the same as a receptacle, one or the other end of the cylinder must be open, and the passages therethrough closed or otherwise to adapt it to its use.

It is possible to incorporate directly in the pessary some particular drug intended for some particular organ or portion of organ. I have shown such a construction in Fig. 7 wherein there is provided in the cup 2 a raised portion 13 which may be a cell containing medicine or drug for the mouth of the uterus or cervix. In dotted lines I have shown an alternative portion 14 intended to enter the cervical canal, and at 15 a longer portion intended to enter the uterus. In each case the drug will be delivered in the organ for which it is intended. To properly insert these types, a physician's services may be necessary.

Figure 11:
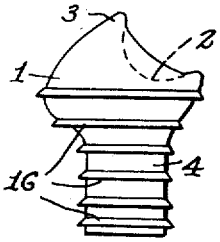
Fig. 11 shows a pessary having a plurality of circumferential flanges.

Instead of the hollow cylinder of Figs. 1, 2, and 3, the same may be made of solid material, and a plurality of downwardly flaring flanges 16 extend from its periphery as shown in Fig. 11, and which prevent the passage of any substance ordinarily entering the hollow cylinder 4.

If desired the device may be air cushioned in whole or in part. This may be done by providing double walls or double bottoms or sides only. If desired the device may be reinforced by rings or ribs both outside and in and these also aid in positioning the device. The cylinder may be of any length or shape to adapt it to its use, and if of removable type may have tapes, strings or gauze incorporated therein to aid in its removal.

What I therefore claim and desire to secure by Letters Patent is:

1. A device of the class described comprising a one-piece member including a head portion having a continuously convex side wall and a concave recess in the upper portion of said head adapted to encircle the os cervix to isolate the same from the vagina, and an integral elongated hollow cylindrical member of lesser diameter than said head member and extending downwardly therefrom, said convex head member being designed to be engaged and closely held by the vagina walls to hold said recess about the cervix and to retain said cylindrical member wholly within the vagina the axis of the cylinder intersecting the axis of the concavity at an angle, said device comprising a consumable material soluble at body temperatures and including a suitable sterilizing medicament freed to all surrounding areas as said material dissolves.

2. A device of the class described comprising a one-piece member including a head portion having a continuously convex side wall and a concave recess in the upper portion of said head adapted to encircle the os cervix to isolate the same from the vagina, a horn extending tangentially from the highest point of the rim of said recess and adapted to enter and fill the fornix, and an integral elongated hollow cylindrical member of lesser diameter than said head member, said convex head being designed to be engaged and closely held by the vagina walls to hold said recess about the cervix and said horn in the fornix, and to retain said cylindrical member wholly within the vagina the axis of the cylinder intersecting the axis of the concavity at an angle, said device comprising a consumable material soluble at body temperatures and including a suitable sterilizing medicament freed to all surrounding areas as said material dissolves.

3. A device of the class described comprising a one-piece member including a head portion having a continuously convex side wall and a concave recess in the upper portion of said head adapted to encircle the os cervix to isolate the same from the vagina, and an integral elongated hollow cylindrical member of lesser diameter than said head member, said convex head member being designed to be engaged and closely held by the vagina walls to hold said recess about the cervix and to retain said cylindrical member within the vagina the axis of the cylinder intersecting the axis of the concavity at an angle, said device consisting of consumable material soluble at body temperatures and including a suitable sterilizing medicament freed to all surrounding areas as said device dissolves.

4. A device as defined in claim 1 consisting of a frame member having on all its surfaces a coating of said consumable soluble medicated material and including a suitable sterilizing medicament freed to all surrounding areas as said coating dissolves.

5. A device as defined in claim 3 in which a naturally expansible consumable packing is disposed within said device and which is freed within the vagina when the device dissolves and swells therein and supports the vagina walls until absorbed by the same.

6. A device as defined in claim 3 in which an absorbent packing is disposed within said device to be freed in the vagina upon solution of the soluble member and means for removing said packing from the vagina.

7. A device as defined in claim 3 in which a member of predetermined design and of consumable medicated material extends from the inner wall of said recess and is adapted to be positioned adjacent the os cervix.

8. A device as defined in claim 3 in which means are provided on the outer wall of the member for entrapping and retaining matter within the vagina until the same is sterilized by the medicament freed as said device dissolves.

9. A device as defined in claim 3 in which there is a continuous passage through said device from said cylindrical member to some predetermined point to permit treatment thereof while other portions of the vagina are protected by the walls of said device.

10. The device claimed in claim 1, in which a member of predetermined design extends from said inner wall of said recess and is adapted to be positioned within the os cervix.

11. The device claimed in claim 1 in which means are provided on the outer wall thereof for entrapping and retaining matter within the vagina until the same is sterilized by the medicament freed as said material dissolves.

12. The device claimed in claim 1 in which there is a continuous passage through said device from said cylindrical member to some predetermined point to permit treatment at such point while other portions of the vagina are protected by the walls of said device.

13. A device of the class described comprising a one-piece member including a head portion having a continuously convex side wall and a concave recess in the upper portion of said head adapted to encircle the os cervix to isolate the same from the vagina, and an integral elongated hollow cylindrical member of lesser diameter than said head member and extending downwardly therefrom and communicating with said head portion and closed at its bottom, said device comprising a consumable material soluble at body temperatures and including a suitable sterilizing medicament freed to all surrounding areas as said material dissolves.

14. The device of claim 13 which consists of a frame having a coating of said consumable solution medicated material.

15. The device of claim 13 in which either the head or cylinder portion is extensible.

16. A device as defined in claim 3, said material being of the class of tapioca or sago.

17. A device as defined in claim 3, said material being of sponge-like texture.

18. A device as defined in claim 3, air being sealed in said body.

19. A pessary for vaginal use comprising a generally cylindrical positioning member of a size to be engaged by the vagina walls, and a generally spherical head member surmounting said cylindrical member and of a size larger than the upper end of the vagina in unextended condition, a depression in the upper and outer side of said head member for surrounding and isolating the os cervix from the vagina, said head member being of greater diameter than the cylindrical member to prevent matter passing between the walls of the vagina and the cylinder from reaching the portion of the head member isolating the os cervix from the vagina, the axis of said depression in said head member isolating the os cervix from the vagina intersecting the axis of the cylinder at an angle, said pessary being composed of a material wholly soluble at body temperatures, said material being of sufficient body and rigidity to maintain the general structural shape of the pessary during and after insertion and prior to being consumed within the vagina, but deformable under pressure of the vagina walls to conform to the contours of the vagina, and a medicament sealed in a pocket within the pessary and released in the vagina as the pessary dissolves to sterilize all matter therein.

20. The pessary of claim 19, said cylinder being hollow, said hollow being sealed from the os cervix-isolating portion of the head member and of a size to entrap matter entering the vagina, said matter being held out of contact with the vagina walls by the wall of said hollow cylinder, and being sterilized as said cylinder dissolves.

21. The pessary of claim 19, said pessary being made in one piece, said cylinder being hollow, said hollow being sealed from the os cervix-isolating portion of the head member and a passage leading through said hollow cylinder to some predetermined point other than the os cervix isolating portion of the head to permit treatment at such point while surrounding areas are protected and sterilized by the material of the walls of said pessary.

22. The pessary of claim 19, the lower side of said head member being concaved to permit ready reformation in said area under pressure of the vagina walls, and said cylinder being centered on said concavity.

RUTH W. MUNRO.